United States Patent
Emenaker et al.

[11] Patent Number: 5,830,296
[45] Date of Patent: Nov. 3, 1998

[54] METHOD FOR SIMULTANEOUSLY EMBOSSING AND FORMING A PERIMETER SEAL ON AN ABSORBENT ARTICLE

[75] Inventors: Ralph Robert Emenaker, Hamilton; Letha Margie Hines, Cincinnati, both of Ohio

[73] Assignee: The Procter & Gamble Company, Cincinnati, Ohio

[21] Appl. No.: 640,201

[22] Filed: Apr. 30, 1996

Related U.S. Application Data

[63] Continuation-in-part of Ser. No. 383,550, Feb. 3, 1995, which is a continuation of Ser. No. 122,114, Sep. 16, 1993, abandoned, and a continuation-in-part of Ser. No. 514,165, Aug. 11, 1995, Pat. No. 5,569,231, which is a continuation of Ser. No. 339,511, Nov. 14, 1994, Pat. No. 5,460,623, which is a continuation of Ser. No. 204,821, Mar. 1, 1994, abandoned.

[51] Int. Cl.$^6$ .......................... A61F 13/15; A61F 13/50; B32B 31/04; B32B 31/20
[52] U.S. Cl. ...................... 156/219; 156/209; 156/220; 156/251; 604/380
[58] Field of Search ............................ 156/209, 219, 156/220, 553, 581, 582, 251; 604/385.1, 387, 366, 370, 380

[56] References Cited

U.S. PATENT DOCUMENTS

| | | |
|---|---|---|
| D. 254,099 | 2/1980 | Richards . |
| 3,494,001 | 2/1970 | Banks . |
| 4,059,114 | 11/1977 | Richards . |
| 4,075,382 | 2/1978 | Chapman et al. ............... 156/219 X |
| 4,184,902 | 1/1980 | Karami . |
| 5,415,918 | 5/1995 | Lang et al. . |
| 5,460,623 | 10/1995 | Emenaker et al. . |
| 5,484,505 | 1/1996 | Isakson et al. . |

FOREIGN PATENT DOCUMENTS

| | | |
|---|---|---|
| 0 072948 A1 | 3/1983 | European Pat. Off. . |
| 0 235 854 A1 | 9/1987 | European Pat. Off. . |
| 2 288 412 | 10/1995 | United Kingdom . |
| WO 95/17148 | 6/1995 | WIPO . |

*Primary Examiner*—Adrienne Johnstone
*Attorney, Agent, or Firm*—Matthew P. Fitzpatrick; Jeffrey V. Bamber; Steven W. Miller

[57] ABSTRACT

A method and apparatus of embossing a pattern into absorbent articles such as sanitary napkins, panty liners, and adult incontinence pads which simultaneously forms a perimeter seal on the absorbent article is disclosed. The method and apparatus utilize a heated sealing member and an anvil surface. The heated sealing member has a recessed region with a lower temperature and lower pressure embossing member therein.

1 Claim, 3 Drawing Sheets

METHOD FOR SIMULTANEOUSLY EMBOSSING AND FORMING A PERIMETER SEAL ON AN ABSORBENT ARTICLE

This application is a continuation-in-part U.S. patent application Ser. No. 08/383,550, which was filed on Feb. 3, 1995, which is a continuation of U.S. patent application Ser. No. 08/122,114, which was filed on Sep. 16, 1993, now abandoned and a continuation-in-part of U.S. patent applicaton Ser. No. 08/514,165, which was filed on Aug. 11, 1995 (now U.S. Pat. No. 5,569,231), which is a continuation-in-part of U.S. patent application Ser. No. 08/339,511, which was filed on Nov. 14, 1994 (now U.S. Pat. No. 5,460,623), which was a continuation of U.S. patent application Ser. No. 08/204,821, which was filled on Mar. 1, 1994, now abandoned.

FIELD OF THE INVENTION

This invention relates to a method and apparatus of embossing a pattern into absorbent articles such as sanitary napkins, panty liners, and adult incontinence pads which simultaneously forms a perimeter seal on the absorbent article.

BACKGROUND OF THE INVENTION

All manner and variety of absorbent articles configured for the absorption of body fluids such as menses, urine, and feces are, of course, well known. One particularly preferred absorbent article is described in U.S. Pat. No. 5,460,623 entitled "Trisection Sanitary Napkin" issued to Emenaker, et al. Another particularly preferred absorbent article is described in PCT Publication No. WO 94/10045, entitled "Sanitary Napkin Having Core Predisposed to a Convex Upward Configuration", published on Mar. 23, 1995 in the name of Letha M. Hines, et al.

The latter publication discloses providing the sanitary napkin with one or more lines of weakness that allow the sanitary napkin to bend in a preferred manner. The lines of weakness may be comprised of discrete embossment sites. In the manufacture of such absorbent articles, difficulties are often encountered in achieving registration of the embossing patterns used to form the line(s) of weakness within the overall sanitary napkin, particularly when the sanitary napkin is being made in a high speed manufacturing operation.

Therefore, it is an object of the present invention to provide a method and apparatus for making an absorbent article, such as a sanitary napkin, which has a pattern of embossments therein. It is another object of the present invention to provide such a method and apparatus which provides a high degree of control over the registration of the embossing patterns, particularly when the sanitary napkin is being made in a high speed manufacturing operation.

These and other objects of the present invention will be more readily apparent when considered in reference to the following description and when taken in conjunction with the accompanying drawings.

SUMMARY OF THE PRESENT INVENTION

The present invention is directed to a method and apparatus of embossing a pattern into absorbent articles such as sanitary napkins, panty liners, and adult incontinence pads which simultaneously forms a perimeter seal on the absorbent article.

The method of the present invention preferably comprises the steps of:

providing the components for an absorbent article, wherein the components have been arranged in preparation for embossing a pattern into at least some of the components and for forming a perimeter seal at least partially around the perimeter of at least some of the components;

providing the apparatus of the present invention, the apparatus comprising a heated sealing member and an anvil surface wherein the heated sealing member has an embossing surface formed therein, and the embossing surface lies within a recessed portion of the heated sealing member and comprises at least one raised portion extending therefrom to form the embossments; and simultaneously embossing and forming a perimeter seal in the components for an absorbent article by placing the components for the absorbent article between the heated sealing member and the anvil surface, and applying pressure to the components while the components are between the heated sealing member and the anvil surface so that the heated sealing member forms a perimeter seal at least partially around the perimeter of at least some of the components, and the embossing surface forms a pattern of embossments into at least some of the components.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which:

DETAILED DESCRIPTION OF THE INVENTION

The present invention is directed to a method and apparatus of embossing a pattern into absorbent articles such as sanitary napkins, panty liners, and adult incontinence pads which simultaneously forms a perimeter seal on the absorbent article.

Figure 1:
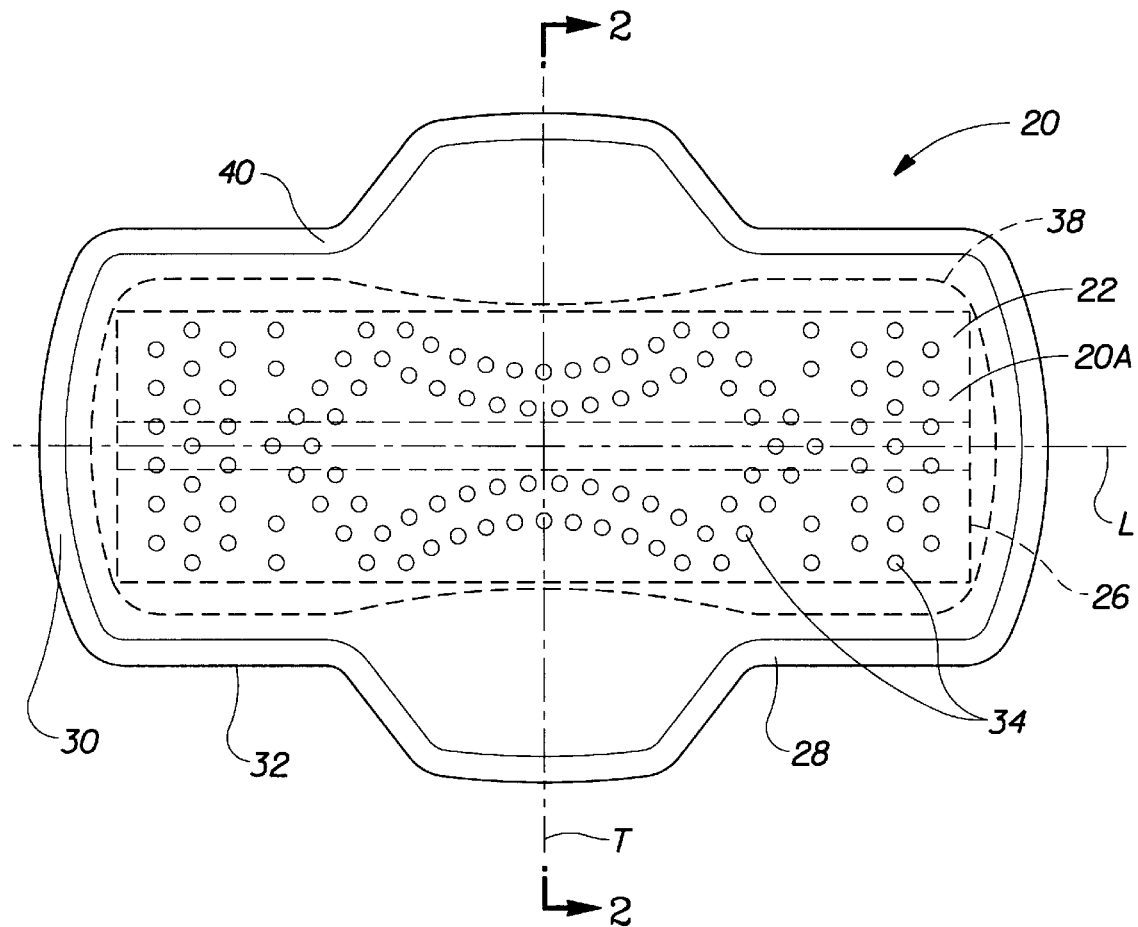
FIG. 1 is a top plan view of a sanitary napkin made using the method and apparatus of the present invention.
Figure 2:
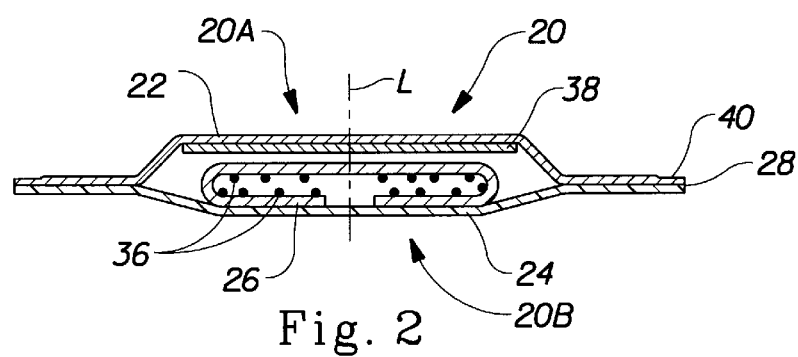
FIG. 2 is a cross-sectional view of the sanitary napkin shown in FIG. 1 taken along line 2—2 of FIG. 1.

FIG. 1 shows one preferred embodiment of a disposable absorbent article made using the process and apparatus of the present invention, sanitary napkin 20. The sanitary napkin 20 has two surfaces, a liquid pervious body-contacting surface or "body surface" 20A and a liquid impervious garment surface 20B. The sanitary napkin 20 is shown in FIG. 1 as viewed from its body surface 20A. As shown in FIG. 2, the sanitary napkin 20 basically comprises a liquid pervious topsheet 22, a liquid impervious backsheet 24, and an absorbent core 26 positioned between the topsheet 22 and the backsheet 24.

The sanitary napkin 20 has two centerlines, a principal longitudinal centerline L and a principal transverse centerline T. The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" used herein, are interchangeable, and refer to a line, axis or direction which lies within the plane of the sanitary napkin 20 that is generally perpendicular to the longitudinal direction. The sanitary napkin 20 has two spaced apart longitudinal edges 28, two spaced apart transverse or end edges (or "ends") 30, which together form the periphery 32 of the sanitary napkin 20.

The sanitary napkin 20 can be of any thickness, including relatively thick, intermediate thickness, relatively thin, or even very thin or "ultra" thin. The embodiment of the sanitary napkin 20 shown in FIG. 1 is intended to be an example of an ultra thin sanitary napkin similar to that described in U.S. Pat. No. 5,460,623 entitled "Trisection Sanitary Napkin" issued to Emenaker, et al. which is provided with a pattern of embossments 34 which can function like those described in U.S. patent application Ser. No. 08/383,550, filed Feb. 3, 1995 (PCT Publication No. WO 94/10045, Hines, et al.). It should be understood that the sanitary napkin shown is merely one preferred embodiment, and that the present invention is not limited to making absorbent articles of the type or having the specific configuration shown in the drawings. For example, the sanitary napkin 20 can also be provided with embossed channels such as those described in U.S. Pat. Nos. 5,234,422 and 5,308,346 issued to Sneller, et al., either in addition to, or as an alternative to the pattern of embossments.

Suitable materials for the various components of the sanitary napkin 20 shown in FIG. 1 are described in greater detail in U.S. Pat. No. 5,460,623 issued to Emenaker, et al. and in the patent publications which are incorporated by reference herein. Preferably, the materials comprising at least the topsheet and backsheet are thermoplastic. In a particularly preferred embodiment, the topsheet 22 comprises the apertured thermoplastic film sold on sanitary napkins by The Procter & Gamble Company of Cincinnati, Ohio, under the trademark DRI-WEAVE, which is manufactured under U.S. Pat. No. 4,342,314 issued to Radel, et al. on Aug. 3, 1982, and U.S. Pat. No. 4,463,045 issued to Ahr, et al. on Jul. 31, 1984. In one particularly preferred embodiment, the absorbent core 26 comprises the absorbent core described in U.S. Pat. No. 5,460,623 issued to Emenaker, et al. The absorbent core 26 preferably comprises absorbent gelling material particles 36. The backsheet 24 preferably comprises a polyethylene film. Preferably, the sanitary napkin 20 further comprises an optional secondary topsheet 38 positioned between the topsheet 22 and the absorbent core 26.

The sanitary napkin 20, as shown in FIG. 2, is assembled in a sandwich configuration in which the topsheet 22 and the backsheet 24 have length and width dimensions generally larger than those of the absorbent core 26. The topsheet 22 and the backsheet 24 extend beyond the edges of the absorbent core 26 and are joined together along a seal 40 to form at least portions of the periphery 32 of the sanitary napkin 20. Since the topsheet 22 and backsheet 24 preferably both comprise thermoplastic material, the seal 40 is formed by crimping or fusing together at least a portion of the parts of the topsheet and backsheet which extend beyond the edges of the absorbent core.

Figure 3:
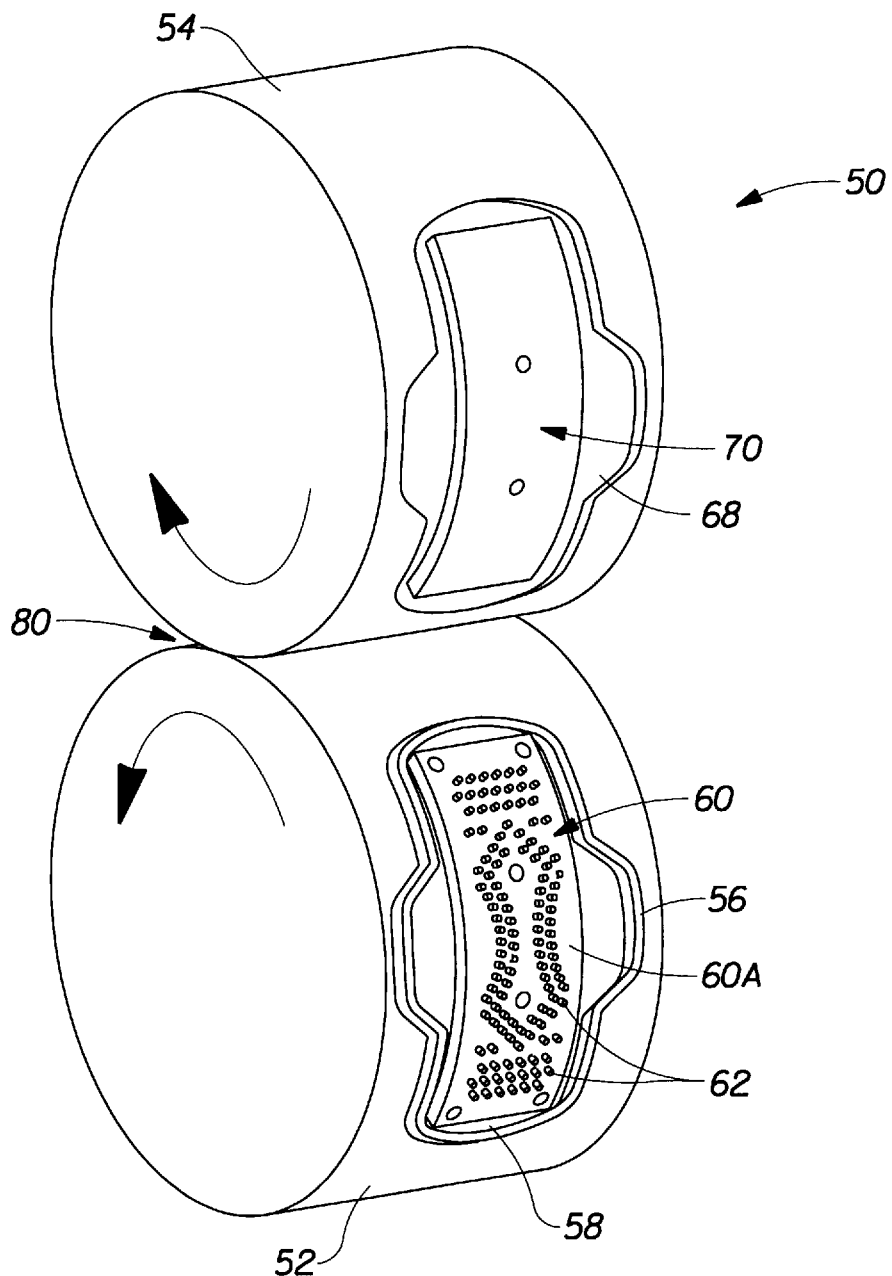
FIG. 3 is a perspective view of an apparatus used to carry out the method of the present invention.

FIG. 3 shows an apparatus 50 used to carry out the method of the present invention. The apparatus 50 shown in FIG. 3 basically comprises a die, which is preferably in the form of die roll 52, and an anvil surface, such as anvil roll 54. The die roll 52 and the anvil roll 54 are preferably both made of a hard metal, such as steel. The die roll and anvil roll are also preferably both heated. The surface temperature of these rolls preferably ranges between about 200°–300° F. (about 90°–150° C.), and is preferably about 250° F. (120° C.). These temperatures are suitable for forming a perimeter seal, but are too high for forming embossments in the components of the absorbent article described herein. Such high temperatures will risk burning a hole through the absorbent article during the embossing process. Thus, a unique arrangement or configuration of the rolls is provided.

Figure 4:
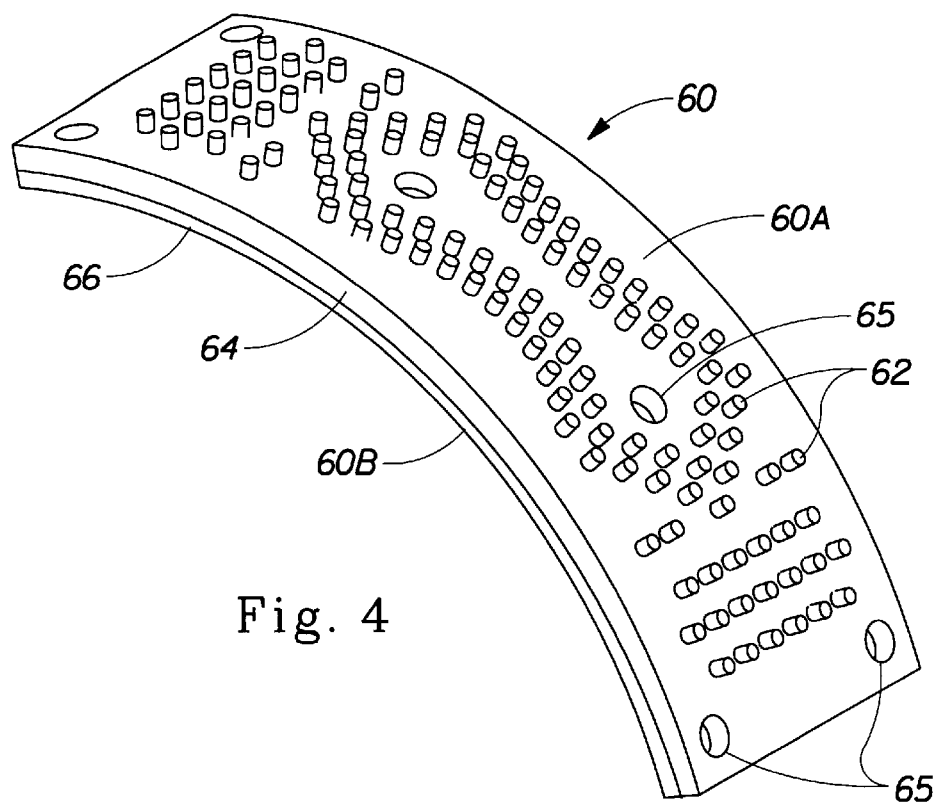
FIG. 4 is an enlarged perspective view of the die roll insert for the apparatus shown in FIG. 3.

The die roll 52 preferably comprises a raised heated sealing surface (or seal-forming region) 56. The seal-forming region 56 is used to form the perimeter seal 40 on the sanitary napkin 20. The die roll 52 further comprises a recessed region 58 with an embossing member 60 therein. The recessed region 58 allows the apparatus 50 to accommodate the added thickness of the absorbent core in the central area of the sanitary napkin, and ensures that this region of the sanitary napkin is not contacted by the heated surface of the rolls. The embossing member 60, shown in greater detail in FIG. 4, comprises an embossing surface 60A with at least one raised portion 62 extending therefrom. Preferably, as shown in FIG. 4, the surface 60A of the embossing member 60 has a plurality of raised portions 62. The raised portions 62 will be used to form embossments 34 in the body surface 20A of the sanitary napkin 20.

The embossing member 60 can be provided in any suitable form. Preferably, the embossing member 60 is in the form of a removable insert. The embossing insert 60 is preferably provided with several bolt holes 65 so that it can be removably affixed to the die roll 52. This allows the embossing member 60 to be easily replaced when worn. It also provides the flexibility to change the pattern of embossments by replacing the removable insert with a different insert. In other embodiments, the embossments 34 can be eliminated from the absorbent article altogether by simply removing the embossing insert 60.

The embossing insert 60 preferably comprises a curved metal (steel) shell 64 that is about 0.25 inches (0.64 cm) thick. The surface 60A of the embossing insert 60 and the raised portions 62 thereon are preferably plasma coated (that is, hard coat annodized with Teflon impregnate according to technologies well known in the art) to avoid build up of glue from the sanitary napkins on the same. In order to avoid burning a hole through the absorbent article, the removable embossing insert 60 also comprises an inner layer 66 of insulating material. The inner layer 66 of insulating material is preferably in the form of a curved Nylon shell that will fit adjacent to the portion of the die roll 52 to which the embossing insert 60 is connected. Thus, the inner layer 66 will be located between the portion of the heated die roll 52 to which the embossing insert 60 is affixed and the embossing surface 60A. The inner layer 66 is capable of insulating the embossing surface 60A from at least some of the heat used to form the perimeter seal 40. The Nylon shell 66 is preferably between about 0.100 and 0.300 inches (about 0.25 and 0.76 cm) thick. The exact thickness is determined by the amount of heat needed to produce the desired embossments.

Figure 5:
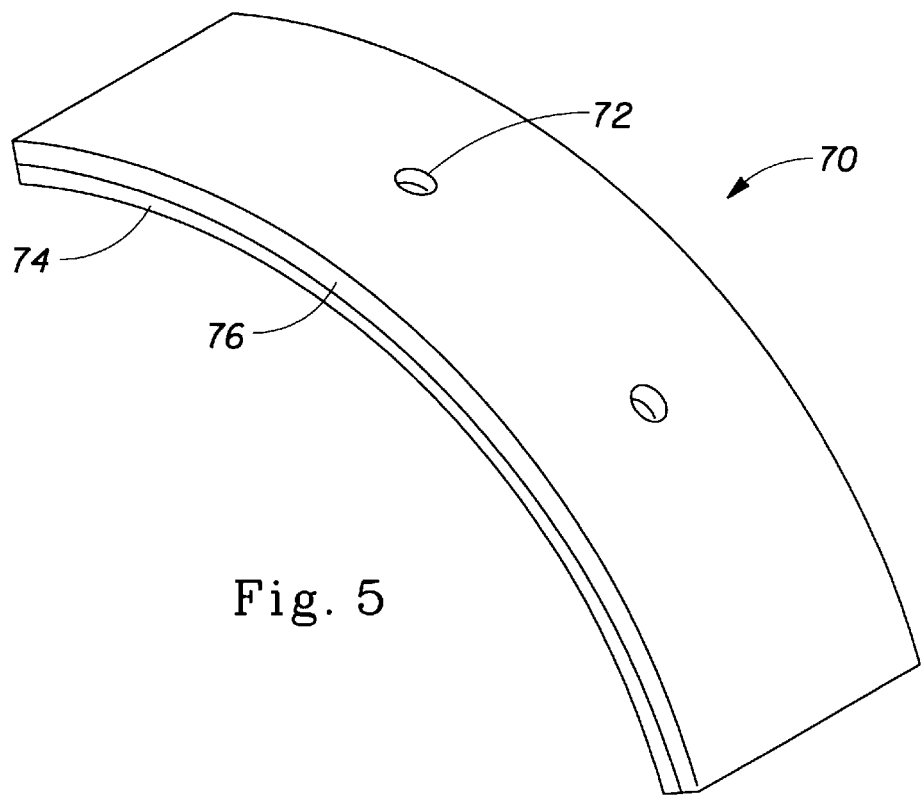
FIG. 5 is an enlarged perspective view of the anvil roll insert for the apparatus shown in FIG. 3.

The anvil roll 54 preferably also has a recessed region 68 having an anvil insert 70 therein. The anvil insert 70 is shown in greater detail in FIG. 5. The anvil insert 70 is provided with a pair of bolt holes 72 so that it is preferably also removable. The anvil insert 70 has a substantially smooth surface and is fit into the recessed region 68 of the anvil roll 54. The anvil insert 70 is preferably softer than the remaining portions of the surface of the anvil roll 54 so that the raised portions 62 on the embossing insert 60 do not rupture the garment facing side of the sanitary napkin 20. The portions of the anvil roll 54 outside of the anvil insert 70 may be referred to herein as the "first portion" of the anvil surface, and the softer anvil insert 70 may be referred to as the "second portion" of the anvil surface. The anvil insert 70 and the softer material on its surface can be comprised of any materials suitable for this purpose. The anvil insert 70 preferably comprises a curved metal (steel) shell 74 about 0.25 inches (about 0.64 cm) thick with a molded urethane facing surface 76. The urethane facing surface 76 is about 0.25 inches (about 0.64 cm) thick and preferably has a hardness range of between about 50 Shore "A" and about 70 Shore "D". In the preferred embodiment described herein, the facing surface 76 of the anvil insert 70 preferably has a hardness of 90 Shore "A". In a preferred embodiment, the urethane surface 76 of the anvil insert 70 is comprised of Cynaprene #D-55 polymer with Cynaset A9QM curative available from Air Products and Chemicals, Inc. of Allentown, Pa. The anvil insert 70 need not have an inner layer of insulating material similar to that of the embossing insert 60 because the urethane facing material 76 provides an equivalent heat insulating function.

The die roll 52 and anvil roll 54 are preferably kept a certain distance apart to define a nip 80 between the rolls, through which the components of the sanitary napkin are fed. To form the particular sanitary napkin described herein, the distance between the die and anvil rolls is preferably less than or equal to about 0.025 inches (about 0.064 cm), and most preferably is about 0.015 inches (about 0.038 cm). Feeding these components between the nip 80 between these heated rolls exerts a pressure upon these components which is sufficient to form the embossments 34 and perimeter seal 40 therein.

In operation, the components of the absorbent article (that is, the topsheet, backsheet, and absorbent core) are laid down on top of each other in the proper sequence, and if desired, at least some of these component are secured together at their faces. The components for the absorbent article are preferably provided in the form of a continuous web or laminate (except for the absorbent core and secondary topsheet which are in discontinuous patches or pieces). When the components are supplied to the apparatus 50 shown in FIG. 3, the components will be arranged in a laminate with the web of topsheet material facing downward. The assembled components are then fed into the nip 80 between the die roll 52 and the anvil roll 54. When the components of the absorbent article are fed into the nip 80 between the die roll 52 and the anvil roll 54, the heated sealing member 56 forms a perimeter seal 40 at least partially around the perimeter of at least some of the components, and the raised portions 62 on the embossing surface 60A simultaneously form a pattern of embossments 34 into at least some of the components.

The method of the present invention differs from prior processes in several respects. In prior art methods, the embossing and the perimeter sealing would be performed in separate operations, with the perimeter sealing generally first, and the embossing generally last. These prior methods required separate mechanisms to control registration of crimping and embossing (that is, alignment of the crimped area and embossments relative to the longitudinal and transverse centerlines of the sanitary napkin). Since the crimping and embossing operations occurred in two separate steps, the prior processes suffered from the drawback that the embossing equipment could form embossments which were not centered inside the perimeter of the sanitary napkin 20. It was originally believed that these two processes were too incompatible to combine together because the heat and pressure needed to form the perimeter seal 40 were much too high for an embossing process, and attempting to form embossments under these conditions would burn holes into the absorbent article.

Various alternative embodiments of the method and apparatus of the present invention also exist. For example, the raised heated sealing surface may be configured to form a seal around only a portion of the perimeter of the absorbent article, or to form a seal on some portion of the absorbent article other than the perimeter. In addition, in other embodiments the insulating material could be located to the sides of the inserts (rather than on the underside or outside surface of the same) if the sides of the inserts are the main portions of the inserts that are in contact with the heated rolls. In still other embodiments, the embossing member, the anvil surface, and the insulating materials could be integral portions of the respective die and anvil rolls, rather than removable inserts. Numerous other alternative embodiments are possible.

In addition, in other embodiments the components of the sanitary napkin may be assembled in a variety of different configurations known in the art and embossed and sealed using the method and apparatus of the present invention. Several preferred sanitary napkin configurations are described generally in U.S. Pat. No. 4,321,924, "Bordered Disposable Absorbent Article" issued to Ahr on Mar. 30, 1982; U.S. Pat. No. 4,425,130, "Compound Sanitary Napkin" issued to DesMarais on Jan. 10, 1984; U.S. Pat. Nos. 4,950,264 and 5,009,653, both entitled "Thin, Flexible Sanitary Napkin" issued to Osborn on Aug. 21, 1990 and Apr. 23, 1991, respectively; U.S. Pat. No. B1 4,589, 876, 4,687,478, and 5,267,992 issued to Van Tilburg which disclose sanitary napkins having flaps, and the aforementioned patent applications issued to Sneller, et al.

The disclosures of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the present invention have been illustrated and described, it would be obvious to those skilled in the art that various other changes and modifications can be made without departing from the spirit and scope of the invention.

What is claimed is:

1. A method of making an absorbent article that has a pattern of embossments thereon and a perimeter seal at least partially around the perimeter thereof, said method comprising the steps of:

providing the components for said absorbent article, wherein said components have been arranged in preparation for embossing said pattern of embossments into at least some of said components and for forming said perimeter seal at least partially around the perimeter of at least some of said components;

providing a heated sealing member and an anvil surface wherein said sealing member is heated to a first temperature, said sealing member has an embossing surface formed therein, said embossing surface comprises a recessed portion of said sealing member with at least one raised portion extending therefrom to form said pattern of embossments, said embossing surface is heated to a second temperature, and said second temperature is less than said first temperature; and simultaneously embossing and forming said perimeter seal in said components to make said absorbent article by placing said components for said absorbent article between said heated sealing member and said anvil surface, and applying pressure to said components while said components are between said heated sealing member and said anvil surface so that said heated sealing member forms said perimeter seal at least partially around the perimeter of at least some of said components, and said embossing surface forms said pattern of embossments into at least some of said components.

* * * * *